(12) United States Patent
Sato et al.

(10) Patent No.: US 7,166,582 B2
(45) Date of Patent: Jan. 23, 2007

(54) ANTIALLERGIC COMPOSITION

(75) Inventors: Toshiro Sato, Iwata (JP); Shuichi Kamo, Iwata-gun (JP); Yutaka Ohtani, Iwata-gun (JP); Yasushi Ueno, Yokohama (JP)

(73) Assignee: J-Oil Mills, Inc., Tokyo (JP)

( * ) Notice: Subject to any disclaimer, the term of this patent is extended or adjusted under 35 U.S.C. 154(b) by 0 days.

(21) Appl. No.: 11/187,913

(22) Filed: Jul. 25, 2005

(65) Prior Publication Data

US 2005/0256084 A1 Nov. 17, 2005

Related U.S. Application Data

(62) Division of application No. 10/702,607, filed on Nov. 7, 2003.

(51) Int. Cl.
*A61K 31/715* (2006.01)
*A61K 31/702* (2006.01)

(52) U.S. Cl. .............. 514/54; 514/61; 514/23; 514/861; 536/123.1

(58) Field of Classification Search ........... 514/54, 514/61, 23, 861; 426/634; 536/123.1
See application file for complete search history.

(56) References Cited

U.S. PATENT DOCUMENTS 5,158,775 A * 10/1992 Yazaki et al. ........... 424/45
5,994,326 A 11/1999 Matsuda et al.
6,946,121 B1 * 9/2005 Martinez et al. ........... 424/70.1
2003/0157200 A1 8/2003 Bonte et al.

FOREIGN PATENT DOCUMENTS

| CN | 1223265 A | 7/1999 |
|---|---|---|
| DE | 19736069 A1 | 2/1998 |
| FR | 2 802 414 | 6/2001 |
| JP | 62198694 | 9/1987 |
| JP | 03151854 | 6/1991 |
| JP | A 11-255656 | 9/1999 |
| JP | A 2001-288093 | 10/2001 |
| JP | 2002058451 | 2/2002 |
| WO | WO 200145713 A | 12/1999 |
| WO | WO 00/06115 | 2/2000 |

OTHER PUBLICATIONS

Okada et al. "Effects of Clobetasol Propionate, a Corticosteroid on Hapten-induced Dermatitis in SPF NC/Nga Mice". Oyo Yakuri/Pharmacometrics 59(6) pp. 135-139, 2000.
Okano et al. (Nippon Nogei Kagaku Kaishi (1939), 15, 238-42).
Smiley et al. (Applied and environmental microbiology, (Apr. 31, 1976 (4) 615-7).

* cited by examiner

*Primary Examiner*—Elli Peselev
*Assistant Examiner*—Michael C. Henry
(74) *Attorney, Agent, or Firm*—Oliff & Berridge, PLC

(57) ABSTRACT

The present invention provides a sate and excellent antiallergic composition, and more particularly a preventive and therapeutic composition for atopic dermatitis, including an antiallergic composition blended with stachyose as an effective ingredient, and a medicine, food and beverage containing the composition.

7 Claims, 5 Drawing Sheets
(1 of 5 Drawing Sheet(s) Filed in Color)

DATA ARE EXPRESSED AS MEAN ± S.E OF SIX MICE
* $P < 0.05$
** $P < 0.01$

ANTIALLERGIC COMPOSITION

This is a Division of Application Ser. No. 10/702,607 filed Nov. 7, 2003. The entire disclosure of the prior application is hereby incorporated by reference herein in its entirety.

BACKGROUND OF THE INVENTION

1. Field of the Invention

The present invention relates to an antiallergic composition, particularly to an antiallergic composition usable for daily intake for preventing onset of atopic dermatitis, and medicines, beverages and foods using the composition.

2. Description of the Related Art

Allergic diseases such as atopic dermatitis have caused severe problems in recent years. Atopic dermatitis occurs as dry lichen like eczema, and is an intractable disease accompanying severe itch. While little is known about the mechanism of the onset of eczema of the atopic dermatitis, it has been made clear that the disease is related to allergic reactions type I and type IV. A type I allergy is an immediate allergy mainly related to IgE antibodies, wherein chemical transmitters such as histamine and leukotriene, and enzymes are released upon reaction of allergenic substances (allergens) with IgE on mast cells and basophils to cause inflammatory reactions on the skin. However, type I allergies are considered not to be directly related to lesions of eczema caused by the atopic dermatitis. A type IV allergy is called as a delayed allergy or cell mediated allergy that causes an inflammatory reaction related to lymphocytes, and the onset of the disease takes 24 to 72 hours after sensitization.

Many protective and therapeutic actions have been attempted for preventing atopic dermatitis. Representative examples thereof include (1) an external medication using external medicines such as adrenocortical hormones, and (2) administration of medicines that suppress immediate reactions such as antihistamine agents. However, the effect of medication is not always sufficient depending on the physical conditions of patients, and the medication has a risk of rebound.

In addition, people with allergic physical conditions have been increasing every year. In extreme examples, the allergic symptom is so sever that daily life of the patient is hindered, which leads to social problems. Under these situations, there is an urgency to develop safe and excellent antiallergic medicines to solve the above mentioned problems, particularly prophylactics and medicaments of the atopic dermatitis.

SUMMARY OF THE INVENTION

It Is an object of the present invention to provide a safe and excellent antiallergic composition, particularly preventive and therapeutic compositions of the atopic dermatitis by solving the problems above on allergic diseases.

The inventors have found, through intensive studies for attaining the objects above, that stachyose has an antiallergic action, particularly an action for suppressing atopic dermatitis, and have completed the present invention.

The present invention provides an antiallergic composition comprising stachyose as an effective ingredient.

Stachyose is a tetrasaccharide contained, for example, in soy beans. Stachyose is a hardly digestible oligosaccharide, and has been known as a factor for activating Lactobacillus bifidus known to have an intestinal function controlling drug among intestinal bacteria, and for accelerating absorption of calcium through the digestive intestine. However, the action for suppressing atopic dermatitis as disclosed in the present invention has not been known in the art.

While the content of stachyose in the antiallergic composition is not particularly restricted, a standard of the desirable amount of intake is 1 to 15 g per day. A content of less than 1 g is not so effective, while a content of more than 20 g may induce temporary diarrhea, although it depends on physical conditions.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 1 is a graph showing the scores of dermatitis in the stachyose administration group and control group;

FIG. 2 is a graph showing the scores of dermatitis in the saccharose administration group and control group;

FIG. 3 is photographs of appearances of test mice;

FIG. 4 is a graph showing the IgE levels in the stachyose administration group, and saccharose administration group and control group; and FIG. 5 is a graph showing scores of dermatitis in the stachyose administration group and conrol group in the conventional NC/Nga mice.

DESCRIPTION OF THE PREFERRED EMBODIMENTS

Performance Evaluation Test 1

The performance of stachyose mixed in livestock feeds was evaluated against the dermatitis induced by repeated application of hapten on an NC/Nga mouse frequently used as an atopic dermatitis model animal (M. Okada et al., Oyo Yakuri/Pharmcometrics, vol. 59, 135–139 (2000)).

Test Method

NC/Nga Tnd Crj male mice at six weeks of age (purchased from Nihon Charles River) were habituated for two weeks. The animals decided as healthy were used for the experiments after an observation of general conditions and body weight measurement. The mice were divided into three groups so that the body weight was averaged. One group was composed of nine mice. A purified livestock feed (AIN93G produced by Oriental Yeast Co.) was used as a basic feed. The mice in Group 1 (a control group) was fed with the purified feed, while the mice in Groups 2 and 3 were fed with a feed prepared by adding the test samples as shown In Table 1 in the basic feed.

TABLE 1

| | |
|---|---|
| Group 1 | AIN93G feed |
| Group 2 | AIN93G feed + stachyose 0.5% |
| Group 3 | AIN93G feed + saccharose 0.5% |

Stachyose used in this test was purified to a purity of 98% by ion exchange chromatography after extracting from soybeans with 70% ethanol. Saccharose used in this test was purchased from Wako Junyaku Kabushiki Kaisha.

The mice at eight weeks of age were used for sensation as follows. The abdomen of the mouse anesthetized with ether was dipped with a pair of hair clippers, and a solution of 2,4,6-trinitrochlorobenzene (named as picryl chloride (PiCl) hereinafter) for sensitization was applied on the abdomen after clipping and on the footpad in a proportion of 150

μL/one animal. Induction was started four days after sensitization, and repeated once a week for five weeks. In the induction period, the back of the mouse anesthetized with ether was clipped with a pair of hair clippers, and the PiCl solution (150 μL/one animal) was applied on the clipped back and right and left ears (at the outer and inner sides of each ear). The hair was clipped after the second induction depending on the growth of the hair.

The symptoms of the atopic dermatitis were observed as follows. The skin condition was observed twice a week starting from a day before the first induction, and the following items were evaluated based on the criteria of clinical syndromes of the human atopic dermatitis. Each mouse was photographed on the day of autopsy.

(1) Observed items
  a. pruritus/itching
  b. erythema/hemorrhage
  c. edema
  e. excoriation/erosion
  f. scaring/dryness (2) Evaluation point
  0 no syndrome
  1 mild syndrome
  2 intermediate syndrome
  4 severe syndrome The serum total IgE concentration was measured as follows. The blood was extracted on day four before administration, and on 43 rd day after administration (the day for starting administration is counted as the first day). The blood (200 μL) is sampled from the orbital plexus venosus using a heparinated capillary. The blood sampled was placed in a tube, centrifuged (at about 4° C. and 1660 g for 15 minutes), and IgE in the supernatant was used for the serum total IgE measurement by an enzyme-linked immunosorbent assay (EIA).

The score of dermatitis, serum total IgE concentration, and the average body weight and standard deviation thereof were calculated. The significant difference was evaluated by the Student's t-test. A significance level of 5% was evaluated as significant, and the results of the Student's t-test were expressed by dividing into a level of less than 5% ($P<0.05$) and less than 1% ($P<0.01$).

Results and Discussion

Figure 1:
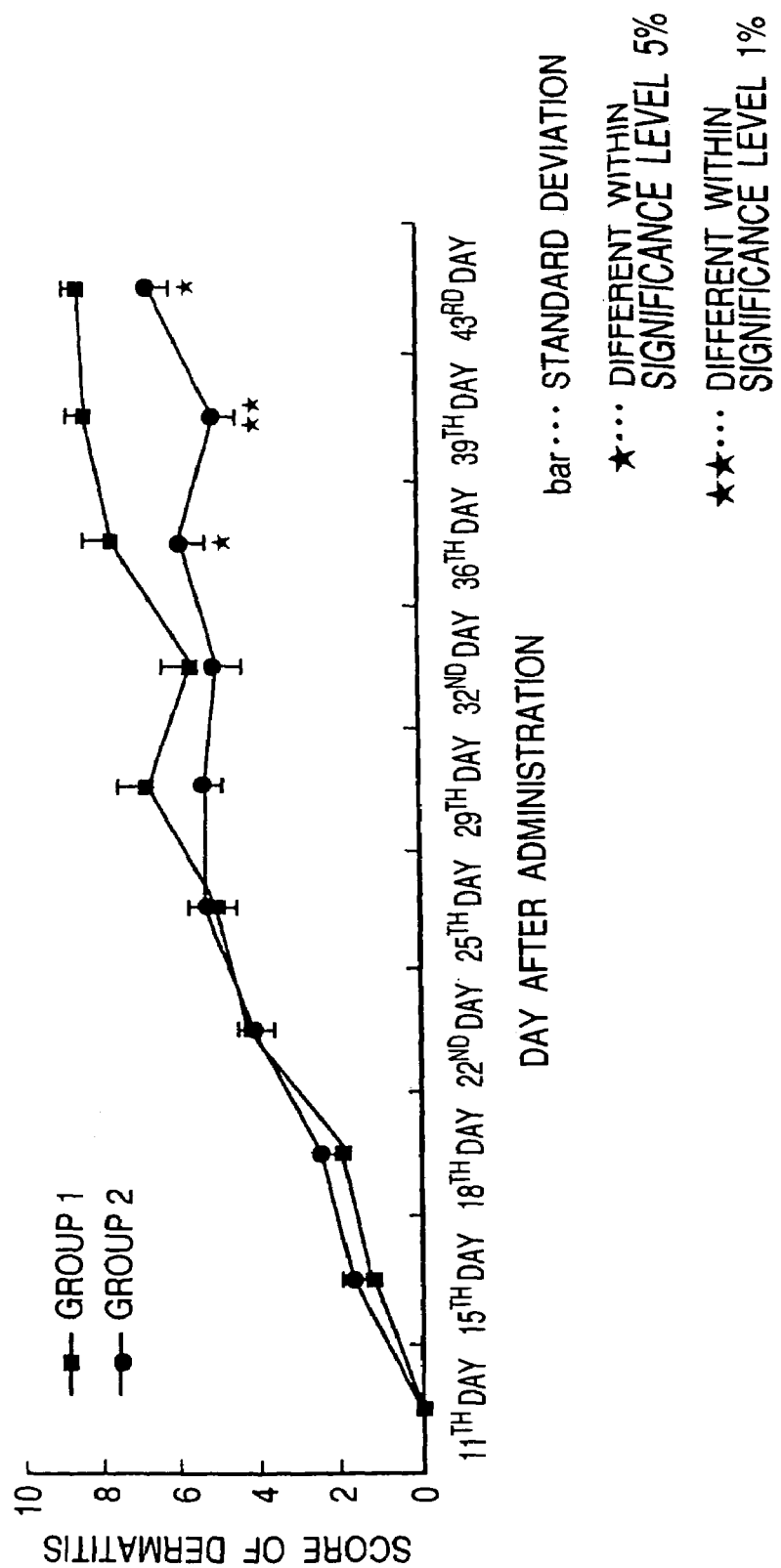
Figure 2:
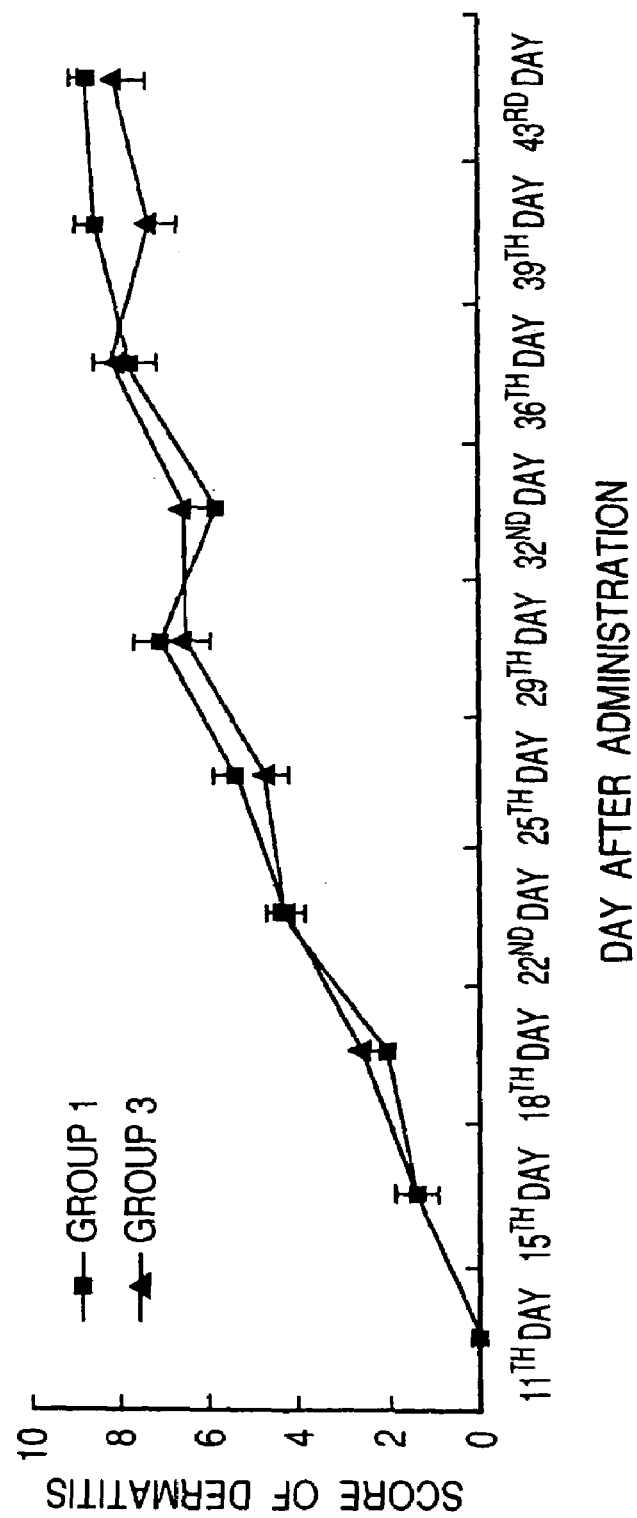
Figure 3:
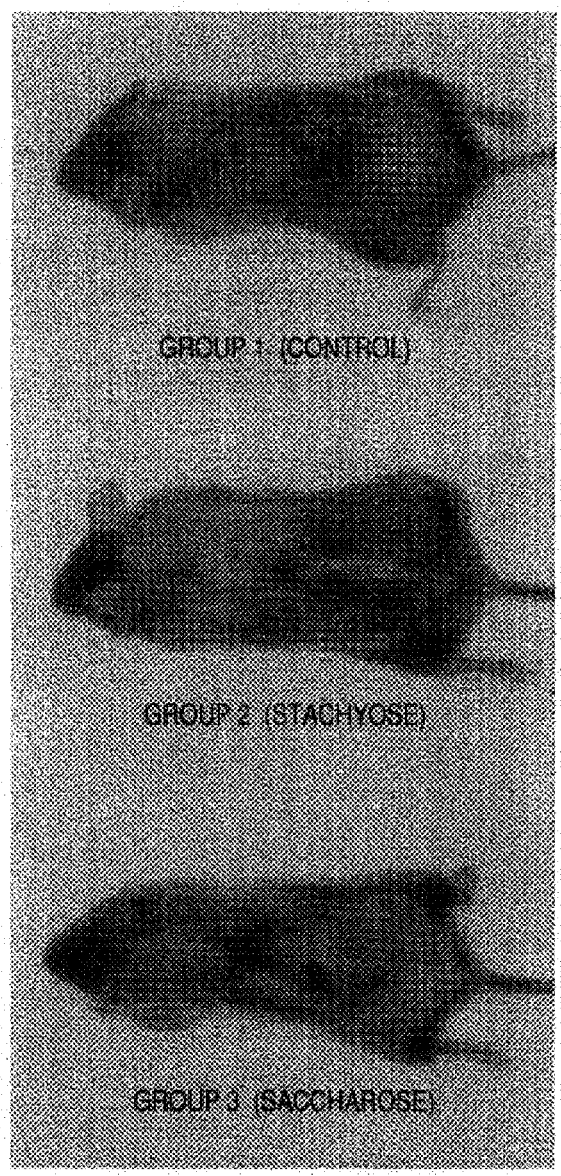

The data of the score of dermatitis are shown in FIGS. 1 and 2. As shown in FIG. 1, progress of the atopic dermatitis was evidently blocked in the stachyose administration group (Group 2). No effects were observed in the saccharose administration group (Group 3) as shown in FIG. 2. The photograph of the appearance of a representative mouse in each group is shown in FIG. 3. An evident difference of the appearance of the skin was observed in the mouse in the stachyose administration group as compared with the mouse in the control group (Group 1).

Figure 4:
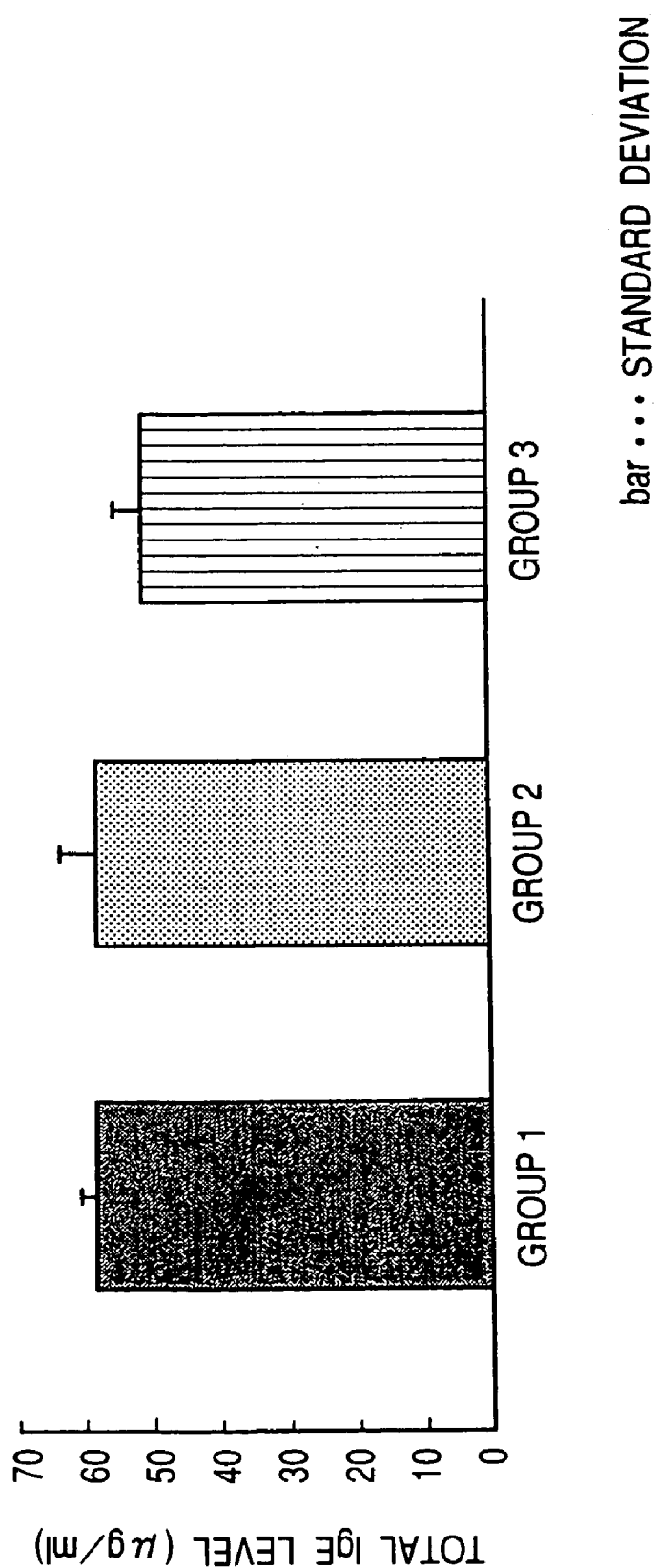

The levels of the serum total IgE as an immediate type (type I) allergy inducing substance are shown in FIG. 4. These levels were not different from the level in the control group.

While the expression mechanism of the anti-atopic dermatitis action of stachyose has not been made clear yet, it may be conjectured that stachyose probably acts on intestinal microorganisms to improve immunity of the digestive intestine. Otherwise, stachyose may directly act on the cells related to immunity of the digestive intestine. While the atopic dermatitis is considered to be related to the immediate allergy and delayed allergy (type IV), it was made clear from the results of the present invention that stachyose has a function against the delayed allergy since stachyose does not influence the level of IgE. While it is known In the art that raffinose as a minute component of the soy bean oligosaccharide has an anti-atopic dermatitis action (Japanese Patent Application Laid-open No. Hei 11-255656), raffinose has an action for suppressing production of IgE (Japanese Patent Application Laid-open No. 2001-288093). Accordingly, the action of stachyose shown in the present invention is evidently different from the action of raffinose.

Performance Evaluation Test 2

The effect of stachyose on the dermatitis was investigated using conventional grade NC/Nga mice that spontaneously start the atopic dermatitis without applying any haptens (H. Matsuda et al., International Immunology, vol. 9, 461–466 (1997)).

(Test method)

Conventional grade female NC/Nga mice at four weeks of age (purchased from Nihon SLC) were habituated for one week. The mice were divided into two groups so that the body weight was averaged. One group was composed of six mice. All the mice were freely fed on the purified livestock feed (AIN93G) before grouping, and the stachyose administration group was fed on a feed supplemented with 1% stachyose after grouping. The skin conditions were observed and evaluated once per two weeks from the day of start of grouping. The evaluation method was the same as in performance evaluation method 1.

(Results)

Figure 5:
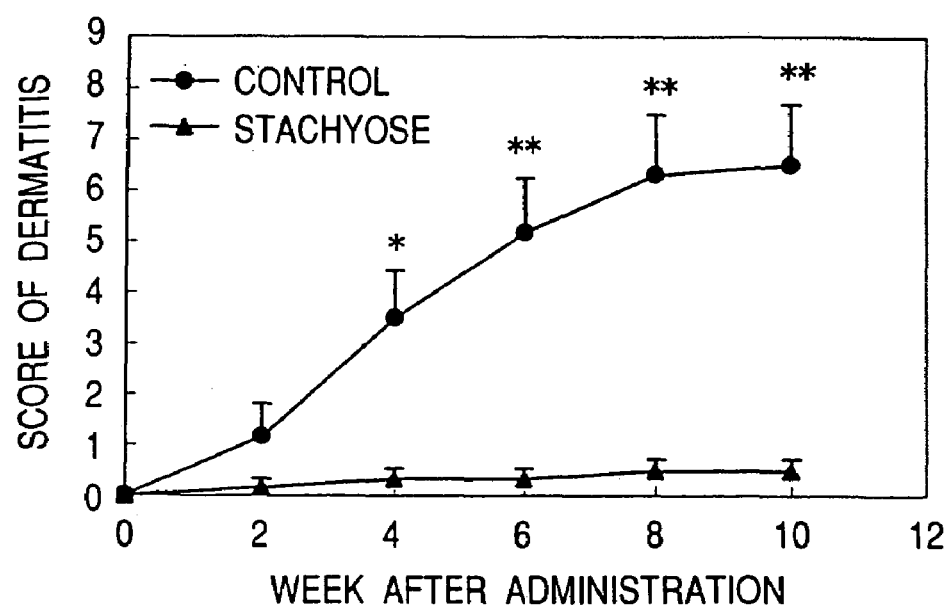

While the dermatitis was observed on the face of five of six mice in the control group on the week four after grouping, no onset of the dermatitis was observed in the stachyose administration group. While evident dermatitis was observed not only on the face but also on the ears in the control group 6 to 8 weeks after grouping, no onset of dermatitis was observed at all in the stachyose administration group. The scores of dermatitis are shown in FIG. 5. The scores of dermatitis show that the effect of stachyose is evident.

The origin and production method of stachyose used in the present invention are not particularly restricted, and any one of natural stachyose, chemically synthesized stachyose and enzymatically synthesized stachyose may be used. However, stachyose originating from soy beans is economically advantageous. Since stachyose is a principal ingredient of the soybean oligosaccharide, the oligosaccharide may be directly used as the stachyose source, or it may be used after purification by ion exchange chromatography.

EXAMPLES

While the present invention is described with reference to examples, the present invention is by no means restricted by the examples as set forth below.

Example 1

| [Ingredient of Capsule] | |
| --- | --- |
| Starting Material | Blend (mg) per 1 Capsule |
| (1) Stachyose | 50 |
| (2) DHA Oil | 50 |

-continued

| [Ingredient of Capsule] | |
|---|---|
| Starting Material | Blend (mg) per 1 Capsule |
| (3) Beefsteak Plant Oil | 50 |
| (4) Bee Wax | 50 |

These materials were capsulated using gelatin after mixing.

Example 2

| [Tablet] | |
|---|---|
| Starting Material | Blend (mg) per 1 Capsule |
| (1) Stachyose | 100 |
| (2) Lactose | 100 |
| (3) Cellulose Powder | 50 |
| (4) Reduced Maltose | 30 |
| (5) Processed Starch | 10 |
| (6) Calcium Carbonate | 1 |

These materials were formulated into tablets after mixing.

Example 3

| [Beverage] | |
|---|---|
| Starting Material | Blend (g) per 1 Bottle |
| (1) Soy Bean Oligosaccharide (Stachyose 50%) | 2 |

-continued

| [Beverage] | |
|---|---|
| Starting Material | Blend (g) per 1 Bottle |
| (2) Sucrose | 10 |
| (3) Coffee Powder | 5 |
| (4) Cow Milk | 183 |

Beverage supplemented with soy bean oligosaccharide and stachyose was produced with sterilization after mixing.

It is evident that the composition blended with stachyose of the present invention exhibits an atopic dermatitis suppressing effect.

What is claimed is:

1. A method of treating allergic diseases, comprising: orally administering stachyose to a patient in need of such treatment.

2. The method according to claim 1, wherein orally administering stachyose comprises administering an amount of stachyose in a range of from more than 1 g to less than 20 g per day.

3. The method according to claim 1, wherein orally administering stachyose comprises administering an amount of stachyose in a range of from more than 1 g to less than 15 g per day.

4. The method according to claim 1, wherein the stachyose is in the form of a capsule or a tablet.

5. The method according to claim 1, wherein the stachyose is in the form of a beverage.

6. The method according to claim 1, wherein the stachyose is effective to suppress symptoms of allergic atopic dermatitis.

7. The method according to claim 1, wherein the stachyose is effective to suppress symptoms of delayed allergy or cell mediated allergy.

\* \* \* \* \*